United States Patent
Macinski (10) Patent No.: US 11,170,394 B1
(45) Date of Patent: Nov. 9, 2021

(54) PARALLEL PROCESSING FOR PHARMACY FULFILLMENT

(71) Applicant: Express Scripts Strategic Development, Inc., St. Louis, MO (US)

(72) Inventor: Christina F. Macinski, St. Charles, MO (US)

(73) Assignee: Express Scripts Strategic Development, Inc., St. Louis, MO (US)

(*) Notice: Subject to any disclaimer, the term of this patent is extended or adjusted under 35 U.S.C. 154(b) by 139 days.

(21) Appl. No.: 16/589,237

(22) Filed: Oct. 1, 2019

Related U.S. Application Data (63) Continuation-in-part of application No. 13/337,649, filed on Dec. 27, 2011, now abandoned.

(51) Int. Cl.
*G16H 20/10* (2018.01)
*G06Q 30/02* (2012.01)

(52) U.S. Cl.
CPC ..... *G06Q 30/0206* (2013.01); *G06Q 30/0201* (2013.01); *G16H 20/10* (2018.01)

(58) Field of Classification Search
CPC ......... G06Q 30/2011; G06Q 50/22–24; G16H 20/10
USPC ............................................................ 705/2
See application file for complete search history.

(56) References Cited

U.S. PATENT DOCUMENTS

| | | | |
|---|---|---|---|
| 2001/0047299 A1 | 11/2001 | Brewer et al. | |
| 2007/0067218 A1 | 3/2007 | Bingham | |
| 2011/0196697 A1 | 8/2011 | Akers et al. | |
| 2012/0185263 A1* | 7/2012 | Emert | 705/2 |

OTHER PUBLICATIONS

"Distributed Computing"; Wikipedia (Year: NA).*
Rider 26 Report, Annual Performance Report for the Prescription Drug Rebate Program, Health and Human Services Commission, Jan. 2009, pp. 1-21.
Rider 40 Report, Semi-Annual Performance Report for the Prescription Drug Rebate Program, Health and Human Services Commission, Mar. 2007, pp. 1-20.
Overview/MedMetrics Health Partners, http://www.medmetricshp.com/products-services/ downloaded May 31, 2012, pp. 1-2.
Reporting & Analytics/Med Metrics Health Partners, http://www.medmetricshp.com/products-services/reporting-analytics.php, downloaded May 31, 2012, pp. 1-2.

* cited by examiner

Primary Examiner — John A Pauls (57) ABSTRACT

Methods and systems for managing pricing guarantees for prescription drugs are described. In one embodiment, a target prescription drug discount guarantee associated with a pharmacy benefit manager client is accessed. A prescription drug discount associated with a plurality of prescription drug claims associated with the pharmacy benefit manager client is calculated to obtain a calculated prescription drug discount. A difference between the target prescription drug discount guarantee and the calculated prescription drug discount is determined. A prescription drug pricing schedule associated with the pharmacy benefit manager client is modified based on the difference between the target discount guarantee and the prescription drug discount to create a modified prescription drug pricing schedule. Other methods and systems are described.

31 Claims, 7 Drawing Sheets

PARALLEL PROCESSING FOR PHARMACY FULFILLMENT

CROSS REFERENCE TO RELATED APPLICATION

This application is a continuation-in-part of U.S. patent application Ser. No. 13/337,649, filed Dec. 27, 2011, which is hereby incorporated by reference in its entirety.

FIELD

The field relates to pharmacy benefit plans, and more particularly to managing pricing guarantees for prescription drugs under pharmacy benefit plans.

BACKGROUND

Pharmacy benefit managers may generally administer prescription drug programs for clients that may, for example, sponsor drug benefit programs for members. As part of the administration of prescription drug programs for clients, pharmacy benefit managers may obtain discount pricing on various prescription drugs that may be utilized by members of drug benefit programs. Pharmacy benefit managers may obtain discount pricing on prescription drugs through various mechanisms, for example through the development of pharmacy networks including retail pharmacies providing negotiated pricing discounts, through rebates from pharmaceutical manufacturers, and through the use of mail order pharmacies that may realize economic efficiencies. As such, pharmacy benefit managers may be able to provide pharmacy benefit plans that may allow members of the pharmacy benefit plan to obtain lower prices for prescription drugs, as compared to full retail pricing for prescription drugs.

DETAILED DESCRIPTION

Example methods and systems for managing pricing guarantees are described. In the following description, for purposes of explanation, numerous specific details are set forth in order to provide a thorough understanding of example embodiments. It will be evident, however, to one of ordinary skill in the art that embodiments of the invention may be practiced without these specific details.

In general, a client engages a pharmacy benefit manager (PBM) to offer a drug benefit program. Examples of clients include governmental organizations (e.g., Federal government agencies, the Department of Defense, the Centers for Medicare and Medicaid Services and state government agencies), middle market companies, large national employers, health insurance companies that have carved out the drug benefit, and the like. A person who is a participant or member of a drug benefit program offered by the client may obtain prescription drugs according to pricing, pharmacy selection, rebates, discounts and the like provided by the terms of the drug benefit program.

The client's offered drug benefit program may be a stand-alone drug benefit operated by the PBM, or as part of a health care benefit operated by a health insurance company where the PBM services are offered directly by the health insurance company or offered indirectly by the PBM on behalf of the health insurance company.

The client typically utilizes the services of the PBM to negotiate and obtain favorable prices for at least some prescription drugs, and/or groups of prescription drugs, that may be purchased by the members, which may assist in reducing the costs to the client for member purchase of prescription drugs. In some embodiments, the PBM may guarantee to the client that the PBM will provide the client with a certain discount on prescription drugs. The discount may be, for example, a discount with respect to a pricing metric such as average wholesale price, an average retail price, or other pricing metric for prescription drugs.

While the PBM may guarantee a certain discount (a target discount guarantee) on prescription drugs to the client for prescription drugs purchased by members, in some instances, the PBM may not be able to obtain pricing on prescription drugs that allow the PBM to achieve the discount guaranteed to the client. In some circumstances (e.g., which may be based on negotiated contractual obligation of the PBM to the client) the PBM may be responsible for reimbursing the client for any difference between a prescription drug discount achieved by the PBM that is less than the target discount guaranteed by the PBM. Example methods and systems for managing pricing guarantees for prescription drugs may allow a PBM to determine the difference between a pricing discount that the PBM actually achieves for prescription drugs, and the target discount guaranteed to the client.

In some embodiments, the methods and systems for managing pricing guarantees for prescription drugs may further enable the PBM to modify the price that will be paid on adjudicated pharmacy claims for prescription drugs purchased by members of the drug benefit program sponsored by the client. The modified pricing may form the basis of the calculating the discount achieved by the PBM, and may allow the PBM to achieve a prescription drug discount that is equal to, or greater than, that target guaranteed discount to the client (e.g., by reducing the amount of the price of the prescription drug covered by the drug benefit program). Reducing the amount of the price of the prescription drug covered by the drug benefit plan may, for example, result in either the client, or the member of the drug benefit program sponsored by the client, having to pay the difference between the cost of the prescription drug and the price paid on adjudicated pharmacy claims.

Figure 1:
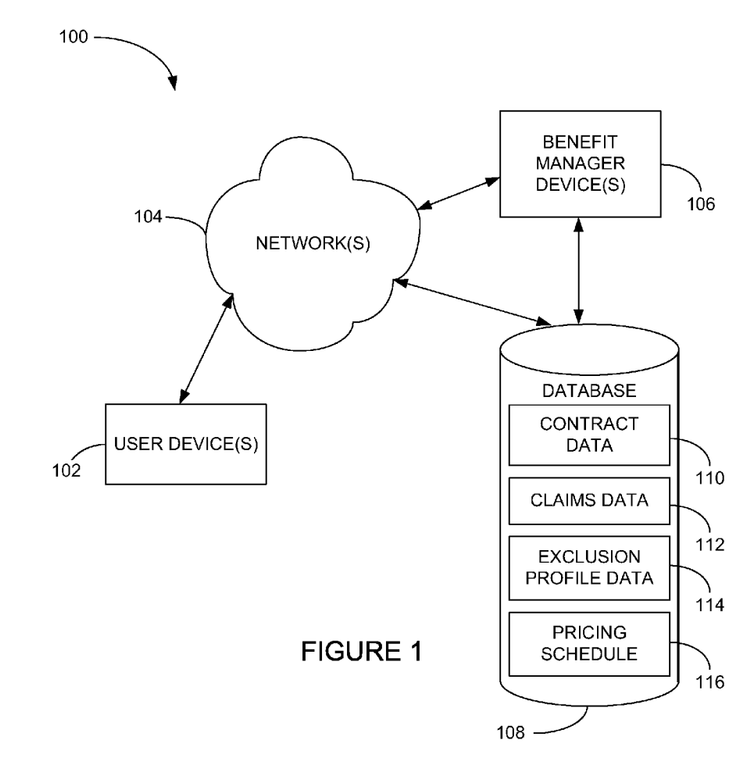
FIG. 1 is a block diagram of an example system, according to an example embodiment.

FIG. 1 is a block diagram of an example system 100, according to an example embodiment. The system 100 is an example embodiment in which a pricing discount for prescription drugs may be managed. The system 100 includes a user device 102 in communication with a benefit manager device 106 over a network 104.

The user device 102 is used by a device operator. The user device 102 may be a stand-alone device that solely provides at least some of the functionality to enable the management of pricing discounts for prescription drugs, or may be a multi-use device that has functionality outside of managing pricing discounts as described herein. Examples of the user device 102 include a set-top box (STB), a receiver card, a mobile telephone, a personal digital assistant (PDA), a display device, a portable gaming unit, and a computing system; however other devices may also be used. For example, the user device 102 may include a mobile electronic device, such an IPHONE or IPAD device by Apple, Inc., mobile electronic devices powered by ANDROID by Google, Inc., and a BLACKBERRY device by Research In Motion Limited. The user device 102 also includes other computing devices, such as desktop computing devices, notebook computing devices, netbook computing devices, gaming devices, and the like. Other types of electronic devices may also be used.

The network 104 by which the user device 102 communicates with the benefit manager device 106 may include, by way of example, Mobile Communications (GSM) network, a code division multiple access (CDMA) network, 3rd Generation Partnership Project (3GPP), an Internet Protocol (IP) network, a Wireless Application Protocol (WAP) network, a WiFi network, or an IEEE 802.11 standards network, as well as various combinations thereof. Network 104 may also include optical communications. Other conventional and/or later developed wired and wireless networks may also be used.

The benefit manager device 106 is a device operated by an entity at least partially responsible for the management of a drug benefit program. While the entity operating the benefit manager device 106 is typically a PBM, other entities may operate the benefit manager device 106 either on behalf of themselves, the PBM, or another entity.

Some of the operations of the PBM that operates the benefit manager device 106 may include the following. A member (or a person on behalf of the member) attempts to obtain a prescription drug at a retail pharmacy location where the member can obtain drugs in a physical store from a pharmacist or pharmacist technician, or in some instances through mail order drug delivery from a mail order pharmacy location.

The member may have a co-pay for the prescription drug that reflects an amount of money that the member is responsible to pay the pharmacy for the prescription drug. The money paid by the member to the pharmacy may come from the personal funds of the member, a health savings account (HSA) of the member or the member's family, a health reimbursement arrangement (HRA) of the member or the member's family, a flexible spending accounts (FSA) of the member or the member's family, or the like. An employer of the member may directly or indirectly fund or reimburse the member or an account of the member for the co-pay.

The amount of the co-pay paid by the member may vary by the benefit plan of the client with the PBM. The member's co-pay may be based on be a flat co-pay (e.g., $10), co-insurance (e.g., 10%), and/or a deductible (e.g., for first $500 of annual prescription drug spend) for certain prescription drugs, certain types of prescription drugs, and/or all prescription drugs.

In certain instances, the member may not pay the co-pay or may only pay for a portion of a co-pay for a prescription drug. For example, if the usual and customary cost for a generic version of a prescription drug is $4, and the member's flat co-pay is $20 for the prescription drug, the member may only pay $4 to receive the prescription drug. In another example involving a worker's compensation claim, no co-pay may be due by the member for the prescription drug.

In conjunction with receiving the co-pay (if any) from the member and dispensing the prescription drug to the member, the pharmacy submits a claim to the PBM for the prescription drug. The PBM may perform certain adjudication functions including verifying the eligibility of the member, reviewing the formulary to determine appropriate co-pay, coinsurance, and deductible for the prescription drug, and performing a drug utilization review (DUR) on the member. The PBM then adjudicates the claim associated with the prescription drug and provides a response to the pharmacy following performance of the aforementioned functions. As part of the adjudication, the client (or the PBM on behalf of the client) ultimately reimburses the pharmacy for filling the prescription drug when the prescription drug was successfully adjudicated. The aforementioned adjudication functions generally occur before the co-pay is received and the prescription drug dispensed. However, the operations may occur simultaneously, substantially simultaneously, or in a different order. In addition, more or fewer adjudication functions may be performed as part of the adjudication process.

The amount of reimbursement paid to the pharmacy by the client and/or member may be based at least in part on the type of pharmacy network in which the pharmacy is included. Other factors may be used to determine the reimbursement amount in addition to the type of pharmacy network.

The user device 102 may be in a client-server relationship with the benefit manager device 106, a peer-to-peer relationship with the benefit manager device 106, and/or in a different type of relationship with the benefit manager device 106.

The benefit manager device 106 may be in communication directly (e.g., through local storage) and/or through the network 104 (e.g., in a cloud configuration or software as a service) with a database 108. The database 108 may be deployed on the user device 102, the benefit manager device 106, both the user device 102 and the benefit manager device 106, partially on the user device 102 and partially on the benefit manager device 106, on a separate device, or may otherwise be deployed. The database 108 may store contract data 110, claims data 112, exclusion profile data 114, and/or a pricing schedule 116.

The contract data 110 includes information regarding contracts between the PBM and one, or more than one, clients of the PBM. In general, the contract data 110 may include information about target discount guarantees provided by the PBM to the client, prescription drugs that are excluded and/or included in the target discount guarantee, and the like. The contract data 110 may include additional information regarding the relationship between the PBM and client including information relating to formulary, prior authorizations, contract term, generic conversion programs, home delivery conversion programs, or the like.

The claims data 112 includes information regarding pharmacy claims adjudicated by the PBM under the drug benefit program provided by the PBM for the client. In general, the claims data 112 includes an identification of the client that sponsors the drug benefit program under which the claim is made, and/or the member that purchased the prescription drug giving rise to the claim, the prescription drug that was filled by the pharmacy, and the price of the prescription drug provided under the drug benefit program. Additional information may be included.

The exclusion profile 116 includes information about what prescription drugs and/or groups of drugs (e.g., by type, such as generic; by classification; and/or by manufacturer, etc.) are excluded from target discount guarantees provided to the client by the PBM. In general, the exclusion profile 116 includes an identification of drugs that are excluded from the target discount guarantees based on the terms of the contract between the PBM and the client. The exclusion profile 116 may be utilized for analyzing pharmacy claims adjudicated by the PBM to determine what claims are subject to the discount guarantee.

The pricing schedule 116 includes a listing of prescription drugs that may be purchased by members of a drug benefit program, and may include a price that the client may be charged for the prescription drugs purchased by members.

While the system 100 in FIG. 1 is shown to include single devices 102, 106, multiple devices may be used. The devices 102, 106 may be the same type of device or may be different device types. When multiple devices are present, the multiple devices may be of the same device type or may be a different device type. Moreover, system 100 shows a single network 104, however, multiple networks can be used. The multiple networks may communicate in series with each other to link the devices 102, 106 or in parallel to link the devices 102, 106.

Figure 2:
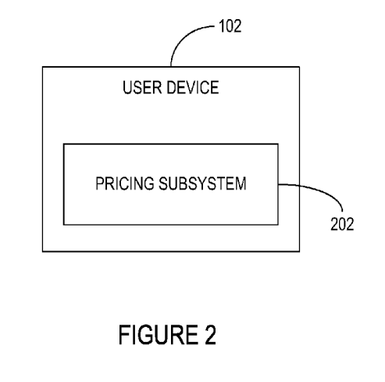
FIG. 2 is a block diagram of an example user device that may be deployed within the system of FIG. 1, according to an example embodiment.

FIG. 2 illustrates the user device 102, according to an example embodiment. The user device 102 may be used by a device operator to manage pricing guarantees, which may include pricing discount guarantees for clients. The user device 102 may be deployed in the system 100, or may otherwise be used.

The user device 102 may include a pricing subsystem 202. The pricing subsystem 202 may enable a prescription drug discount achieved on prescription drugs in qualifying claims for members of a drug benefit program sponsored by a client to be compared with a target discount guaranteed to the client by the PBM. In some embodiments, the pricing subsystem 202 may allow a pricing schedule for prescription drugs, used to determine a price to be paid for prescription drugs under the drug benefit program sponsored by the client to be modified. Modifying the pricing schedule may enable a prescription drug discount pricing achieved based on the modified pricing schedule to meet and/or exceed the target discount guaranteed to the client.

Figure 3:
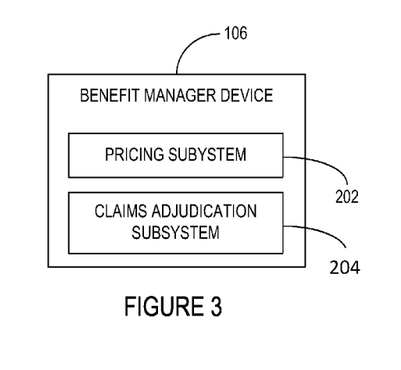
FIG. 3 is a block diagram of an example benefit manager device that may be deployed within the system of FIG. 1, according to an example embodiment.

FIG. 3 illustrates the benefit manager device 106, according to an example embodiment. The benefit manager device 106 may be deployed in the system 100, or may otherwise be used.

The benefit manager device 106 may include the pricing subsystem 202 and claims adjudication subsystem 204. In some embodiments, the pricing subsystem 202 when used may provide server-side functionality to the user device 102. By way of example, the pricing subsystem 202 may be deployed in both the user device 102 and the benefit manager device 106, or in one of the devices 102 or 106. The user device 102 may then perform some of the functionality while other functionality is performed by the benefit manager device 106.

The claims adjudication subsystem 204 may be deployed in the benefit manager device 106, partially deployed in the benefit manager device 106 and partially in another device, or may be completely deployed in another device. The claims adjudication subsystem 204 may be in separate device than the pricing subsystem 202. The claims adjudication subsystem 204 enable certain adjudication functions, for example, verifying the eligibility of the member, reviewing the formulary to determine appropriate co-pay, coinsurance, and deductible for the prescription drug, and performing a drug utilization review (DUR) on the member. The claims adjudication subsystem 204 may also enable a response to be provided to a pharmacy following performance of the aforementioned functions. In some embodiments, the claims adjudication subsystem 204 may enable reimbursement of the pharmacy for filling the prescription drug when the prescription drug was successfully adjudicated.

Figure 4:
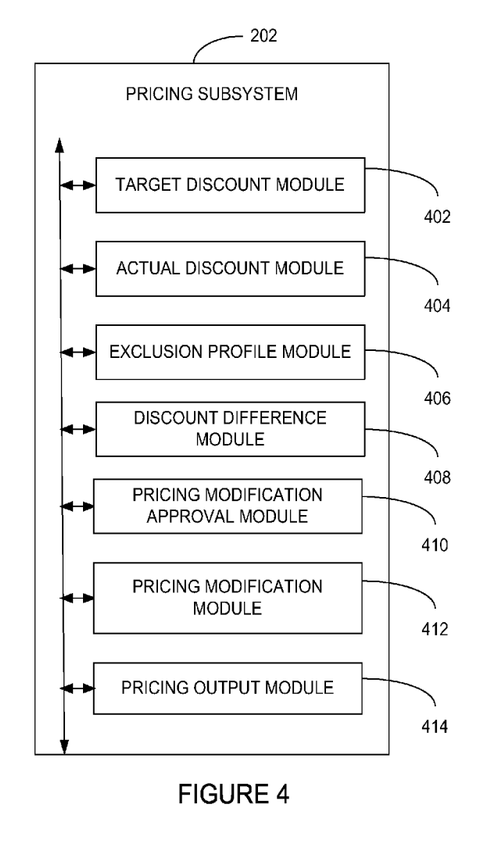
FIG. 4 is a block diagram of an example pricing subsystem that may be deployed within the user device of FIG. 2 or the benefit manager device of FIG. 3, according to an example embodiment.

FIG. 4 illustrates an example the pricing subsystem 202 that may be deployed in the user device 102, the benefit manager device 106, or otherwise deployed in another system. One or more modules are communicatively coupled and included in the pricing subsystem 202 to enable the management of pricing guarantees, which may include discounts provided to clients and control of pricing schedules for prescription drugs offered to clients. The modules of the pricing subsystem 202 that may be included are a target discount module 402, an actual discount module 404, an exclusion profile module 406, a discount difference module 408, a pricing modification approval module 410, a pricing modification module 412, and a pricing output module 414.

In some embodiments, the modules of the pricing subsystem 202 may be distributed so that some of the modules are deployed in the user device 102 and some modules are deployed in the benefit manager device 106. In one embodiment, the modules are deployed in memory and executed by a processor coupled to the memory. The functionality contained within the modules 402-414 may be combined into a lesser number of modules, further divided among a greater number of modules, or redistributed among existing modules. Other configurations including the functionality of the modules 402-414 may be used.

In some embodiments, the target discount module 402 may access the target prescription drug discount guarantee associated with a client. A target discount guarantee may be associated with a single client, or more multiple clients. The target discount guarantee may include the discount on prescription drug prices guaranteed to the client by the PBM. The target discount guarantee may be based on one or more pricing metrics for prescription drugs. For example, the target discount guarantee may be a discount on price for a single prescription drug, or multiple prescription drugs relative to an average wholesale price for the one, or more than one, prescription drug. Other pricing metrics for prescription drugs may additionally and/or alternatively be utilized as the basis for determining the target discount guarantee, such as an average retail price, a pharmacy dispensing fee, or the like.

In some embodiments, the target discount guarantee associated with a client may be based on a contract between the PBM and the client. The contract between the PBM and the client may specify the amount of the target discount guarantee and/or may specify the pricing metric that may form the basis of the target discount guarantee (e.g., a percentage discount relative to the average wholesale price of the prescription drug, or the like). In some embodiments, the target discount guarantee may be different depending upon a class of prescription drug (e.g., brand name drug, and different classes of generic drugs) and a channel of delivery (e.g., retail or mail-order). In some embodiments, other types of drugs, such as specialty drugs, may have additional/ alternative associated target discount guarantees. Accordingly, a target discount guarantee associated with the client may vary depending upon the type of prescription drug, depending upon the channel of delivery, or depending upon both the type of prescription drug and the channel of delivery.

In some embodiments, the target discount module 402 may access the contract data from the database 108. In some embodiments, the target discount module 402 may access the contract data by receiving the contract data 110. Receiving the contract data may include, for example, receiving the contract data through the network 104 from the user device 102, from the benefit manager device 106, or from a different device.

In some embodiments, the actual discount module 404 may calculate a prescription drug discount for one claim, or multiple claims, associated with the client. Generally, the prescription drug discount may include the discount that was actually achieved for a prescription drug with respect to the pricing metric specified in the contract data 110. In some embodiments, the actual discount module 404 may calculate the prescription drug discount of the one claims, or the multiple claims, associated with the client by comparing the price paid for the prescription drugs to a pricing metric (such as an average wholesale price, or other pricing metric, e.g., that may be defined in the contract data 110). In some embodiments, the price paid for the prescription drugs may include the price paid by the member (e.g., in the form of a co-pay, or other payment) and/or by the client (e.g., in the form a balance paid in addition to the co-pay) to the pharmacy, or a mail order cost.

In some embodiments, the actual discount module 404 may calculate the prescription drug discount achieved for one claim, or multiple claims, associated with the client over a period of time. In an example embodiment, the actual discount module 404 may calculate the prescription drug discount achieved on pharmacy claims adjudicated for a client for a one-month period, a three-month period, or another period of time.

In some embodiments, the actual discount module 404 may access the claims data 112 for a defined period of time. The actual discount module 404 may access the claims data 112 from the database 108. In some embodiments, accessing the claims data may include receiving that claims data. Receiving the claims data 112 may include receiving the claims data 112 may include receiving the claims data over the network 104 from the user device 102, from the benefit manager device 106, or from a different device.

The actual discount module 404 may determine what claims included within the claims data 112 are associated with the client. For example, the actual discount module 404 may determine what claims included within the claims data 112 are associated with the client based on a client identifier associated with individual claims included within the claims data 112.

The actual discount module 404 may identify a single claim, or multiple claims, of the claims data 112 that may be used to calculate the prescription drug discount achieved on claims for prescription drugs adjudicated by the PBM on behalf of the client. In some embodiments, the actual discount module 404 may identify one claim, or multiple claims, that may be used to calculate the prescription drug discount by identifying one or more claims that are excluded from the target discount guarantee. In some embodiments, the actual discount module 404 may identify one claim, or multiple claims, that are excluded from the target discount guarantee based on the exclusion profile 114 stored within the database 108. Having identified the one claim, or multiple more claims, that are excluded form the target discount guarantee, the actual discount module 404 may calculate the prescription drug discount achieved for the claims in the defined period based on a difference between the price paid for the prescription drugs included within the target discount guarantee and the pricing metric on which the target discount guarantee is based, for example the average wholesale price of the prescription drugs included within the target discount guarantee.

In some embodiments, the exclusion profile module 406 may access the exclusion profile 114 associated with the client, and may provide the exclusion profile 114 to the actual discount module 404. In some embodiments, the exclusion profile module 406 may determine which claims are excluded from the target discount guarantee, and may exclude those claims from the claims utilized by the actual discount module 404 in calculating the prescription drug discount achieved for claims associated with the client.

In general, the exclusion profile 114 may include a listing of drugs that are excluded from the target discount guarantee. In some embodiments, the drugs that are excluded from the target discount guarantee may be based upon the contract data 110. In some embodiments, the exclusion profile module 406 and/or the actual discount module 404 may determine claims that are excluded from calculating the prescription drug discount by excluding claims for drugs that listed in the exclusion profile 114. In general, excluded drugs may include drugs that may be difficult for the PBM to negotiate favorable pricing on. Examples of drugs that may be excluded from the target discount guarantee may include over the counter drugs, specialty drugs, patent litigated drugs, and single source generic drugs, and the like. In some embodiments, the exclusion profile module 406 may enable the exclusion profile 114 to be modified. For example, the exclusion profile module 406 may enable the exclusion profile to be modified based on changes in the contract data 110, to be modified based on modified interpretations of drugs that should be included within the exclusion profile 114, to be modified based on changes in category of drugs (e.g., if a drug becomes a patent litigated drug), and/or to be modified on another basis.

In some embodiments, the exclusion profile module may access the exclusion profile 114 from the database 108. In some embodiments, accessing the exclusion profile 114 from the database 108 may include receiving the exclusion profile 114 over the network 104 from the user device 102, from the benefit manager device 106, or from a different device.

In some embodiments, the discount difference module 408 may determine the difference between the target prescription drug discount guarantee and the calculated prescription drug discount determined by the actual discount module 404. In general, the discount difference module 408 may determine the difference between the target discount guarantee and the prescription drug discount by comparing the target discount guarantee and the prescription drug discount. In some embodiments, the prescription drug discount may be substantially the same as the target discount guarantee, may be higher than the target discount guarantee, and/or may be lower than the target discount guarantee.

In an example embodiment in which the prescription drug discount may be lower than the target discount guarantee, the pricing modification approval module 410 transmit a difference notification based on the difference between the target prescription drug discount guarantee and the calculated prescription drug discount. The pricing modification approval module 410 may receive approval to modify the pricing schedule 116 in response to the transmission of the difference notification. For example, in some embodiments it may not be desirable to modify the pricing schedule 116, e.g., for business reasons. For example, frequent changes to the pricing schedule 116 may be met with resistance from the client, may alter a relationship between the PBM and the client in an undesired manner, or may otherwise not be desired. Accordingly, in some embodiments, receiving approval to modify the pricing schedule 116 may include receiving approval to modify the pricing schedule 116 and/or may include receiving disapproval to modify the pricing schedule 116.

In some embodiments, the pricing modification approval module 410 may transmit a difference notification based on the difference between the target prescription drug discount guarantee and the calculated prescription drug discount. The pricing modification approval module 410 may receive approval to modify the pricing schedule 116 based on a user selection, e.g., from the user of user device 102. In some embodiments, the pricing modification approval module 410 may receive approval to modify the pricing schedule 116 based on one, or more than one, business rules, or other logic.

The pricing modification module 412 may generally modify the pricing schedule 116 to achieve an increase and/or a decreased prescription drug discount achieved for pharmacy claims associated with the client for non-excluded drugs. For example, if a prescription drug discount calculated by the actual discount module 404 is less than the target discount guarantee, the pricing modification module 412 may modify the pricing schedule 116 to achieve an increase in the prescription drug discount. In some embodiments, the pricing modification module 412 may modify the pricing schedule 116 to achieve a prescription drug discount for anticipated future claims that is equal to the target discount guarantee. In some embodiments, the pricing modification module 412 may modify the pricing schedule 116 to achieve a prescription drug discount for anticipated future claims that is greater than the target discount guarantee by an amount sufficient to offset a calculated prescription drug discount that is less than the target discount guarantee.

In general, the pricing modification module 412 may modify the pricing schedule 116 for drugs included within the target discount guarantee that may change the prescription drug discount to achieve the desired effect (e.g., to increase the prescription drug discount achieved by a desired amount). Accordingly, the pricing modification module 412 may modify the pricing of one, or more than one, prescription drugs included within the pricing schedule 116 to achieve a desired change in the anticipated prescription drug discount (e.g., the actual and/or estimated discount achieved for claims in the future).

In some embodiments, the pricing modification module 412 may determine the drugs included within the target discount guarantee, e.g., by accessing the exclusion profile 114. Accordingly, the pricing modification module 412 may be able to modify pricing associated with drugs that are included within the target discount guarantee. In some embodiments, the pricing modification module 412 may determine what drugs included within the target discount guarantee may impact the prescription drug discount (e.g., based on the number of prescriptions filled for one or more drugs and for a given current pricing of the one or more drugs). In some embodiments, the pricing modification module 412 may determine what drugs included within the target discount guarantee may impact the prescription drug discount based on the claims data 110 (e.g., which may enable the pricing modification module 412 to determine what drugs included within the target discount guarantee are being adjudicated and at what rate), and based on the pricing schedule 116 (e.g., which may enable the pricing modification module 412 to determine the dollar value and/or a prescription drug discount associated with what drugs included within the target discount guarantee).

In some embodiments, the pricing modification module 412 may modify the pricing schedule based anticipated future claims for prescription drugs included within the target discount guarantee. For example, over time claims adjudicated for prescription drugs may remain generally constant if a sufficiently large number of members fill prescriptions under the drug benefit program. However, some variations in the number of claims for prescription drugs included within the target discount guarantee may be predicted based on seasonal drugs (e.g., allergy drugs, and the like), predicted release of new drugs (e.g., which may impact the rate of prescriptions for one or more existing drugs), drugs for which patent protection may be expiring (e.g., which may give rise to competing generic drugs), and the like. Accordingly, in some embodiments the pricing modification module may predict future claims (e.g., for a defined future period of time) based on historical claims adjudicated for prescription drugs and based on predicted changes in claims for prescription drugs.

In an embodiment, the pricing modification module 412 may modify the pricing schedule 116, for example, based on one, or more than one, of the claims data 110, the exclusion profile 114, and predicted changes in future claims adjudicated by the PBM in connection with the drug benefit program to achieve a desired anticipated change in the prescription drug discount achieved for future claims that may be adjudicated in connection with the drug benefit program.

The pricing output module 414 may transmit the modified pricing schedule to a claims adjudication system. In some embodiments, the pricing output module 414 may store the modified pricing schedule 116 in the database 110, on the user device 102, on the benefit manager device 106, and/or in a different location. In some embodiments, the pricing output module 414 may transmit the modified pricing schedule to the claims adjudication system, for example, via network 104, or the like. In addition to other pricing schedules, the modified pricing schedule may include the pricing schedule that may be used by the claims adjudication system of processing future pharmacy claims for prescription drugs included within the pricing schedule. For example, the claims adjudication system may process pharmacy claims for prescription drugs included within the updated pricing schedule in accordance with the prices included within the updated pricing schedule.

Figure 5A:
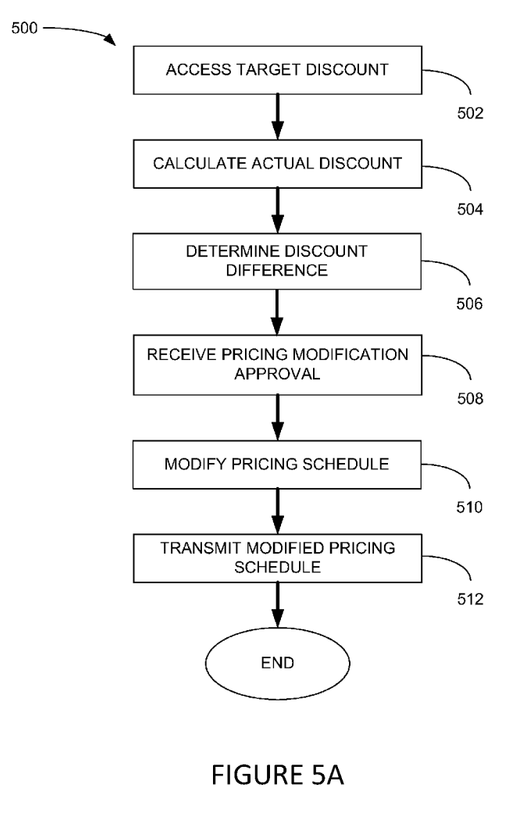
FIG. 5A is a process flow illustrating a method for managing client discounts, according to an example embodiment

FIG. 5A illustrates a method 500 for managing pricing guarantees, according to an example embodiment. The method 500 may be performed by the user device 102, by the benefit manager device 106, partially by the user device 102 and partially be the benefit manager device 106, or may be otherwise performed.

The target discount guarantee associated with a client may be determined at block 502. The target discount guarantee may include the discount on prescription drug pricing, relative to a prescription drug pricing metric, guaranteed to a client of a PBM for prescription drugs purchased by members of a drug benefit program sponsored by the client. The target discount guarantee may be based on a contract between the client and the PBM. The contract between the client and the PBM may indicate what discount on prescription drugs purchased by members is guaranteed for the client, and what drugs are included in the target discount guarantee.

In some embodiments, determining the target discount guarantee may include accessing the contract data 110 from the database 108. In some embodiments, accessing the contract data 110 may include receiving the contract data 110 directly from the database 108, and/or receiving the contract data 110 via the network 104.

A prescription drug discount may be calculated at block 504. The prescription drug discount may be calculated for a time period, such as a one-month time period, a three-month time period, or for another time period. The prescription drug discount achieved by the PBM may be calculated for the drugs included within the target discount guarantee, and relative to the same pricing metric upon which the target discount guarantee is based.

In some embodiments, calculating the prescription drug discount may include accessing the contract data 110. Accessing the claims data 110 may include accessing the claims data 110 from the database 108, and/or receiving the contract data 110 from the database 108, directly, via network 104, or otherwise receiving the contract data. The pricing metric for calculating the prescription drug discount may be determined from the contract data.

In some embodiments, calculating the prescription drug discount may include accessing the claims data 112. Accessing the claims data 112 may include accessing the claims data 112 from the database 108, and/or receiving the claims data 112 from the database 108, directly, via network 104, or otherwise receiving the claims data 112. The claims data 112 may include the claims adjudicated by the PBM during the time period that are associated with the client, with respect to whom the prescription drug discount is calculated. The claims adjudicated may indicate what prescriptions were filled during the time period and what price was associated with each prescription filled during the time period.

In some embodiments, calculating the prescription drug discount may include accessing the exclusion profile data 114. Accessing the exclusion profile data 114 may include accessing the exclusion profile data 114 from the database 108, and/or receiving the exclusion profile data 114 from the database 108, directly, via network 104, or otherwise receiving the exclusion profile data 114. The exclusion profile data may indicate what drugs are not included within the target discount guarantee, and may be excluded from the calculation of the prescription drug discount achieved by the PBM.

A difference between the target discount guarantee and the prescription drug discount may be determined at block 506. The difference between the target discount guarantee and the prescription drug discount may be determined based on a comparison between the target discount guarantee and the prescription drug discount achieved by the PBM for pharmacy claims adjudicated during the time period.

A pricing modification approval may be received at block 508. The pricing modification approval may determine whether or not pricing associated with one or more prescription drugs included within the target discount guarantee may be changed. The pricing modification approval may be received based on a user selection and/or based on one, or more than one, business rules or logic. For example, the pricing modification approval may be denied for a client that may be unhappy with the frequency of changes in pricing, or the like.

The pricing schedule 116 associated with one, or more than one, drugs included within the target discount guarantee may be modified at block 510. In general, the pricing schedule 116 may be modified to produce a change in the prescription drug discount achieved by the PBM for claims adjudicated in the future. The pricing schedule 116 may be modified to change the pricing of prescription drugs included within the target discount guarantee. In some embodiments, the pricing schedule 116 may be modified to provide an anticipated future prescription drug discount equal to the target discount guarantee and/or to provide an anticipated future prescription drug discount that is greater than, or less than, the target discount guarantee (e.g., to compensate for a determined difference between the target discount guarantee and the prescription drug discount).

In some embodiments, modifying the pricing schedule 116 may include accessing claims data 112 to determine what drugs historically (e.g., over a time period) have been adjudicated and at what rate (e.g., what frequency). In some embodiments, it may be generally assumed that the drugs adjudicated and the rate of adjudication of the drugs may remain generally constant over time and/or may vary in a pattern over time.

In some embodiments, modifying the pricing schedule 116 may include accessing the exclusion profile data 116 to determine what claims within the claims data 112 may be included within (e.g., by excluding those claims not included within) the target discount guarantee. In some embodiments, modifying the pricing schedule 116 may include modifying the price associated with drugs that may impact an anticipated future prescription drug discount achieved by the PBM.

In some embodiments, modifying the pricing schedule 116 may include modifying the pricing schedule based on anticipated changes in prescriptions for one, or more than one, drugs. For example, one, or more than one, drug may experience seasonal and/or periodic changes in prescription rate (e.g., from a historical perspective). Such changes in prescription rates may be considered in modifying the pricing schedule. In some embodiments, other occurrences anticipated to impact the prescription drug discount may be considered. Such other occurrences may include, for example, anticipate releases of new drugs (e.g., which may be include within the target discount guarantee and/or which may impact the prescription rate and/or price of drugs included within the discount guarantee), drugs for which patent protection may expire (e.g., which may give rise to the introduction of generic equivalents), or the like.

The modified pricing schedule 116 may be output at block 512. Outputting the modified pricing schedule 116 may include storing the modified pricing schedule 116 to the database 108. In some embodiments, outputting the modified pricing schedule 116 may include providing (e.g., transmitting or otherwise making available) the modified pricing schedule to a claims adjudication system, for example, for use in adjudicating future pharmacy claims.

Figure 5B:
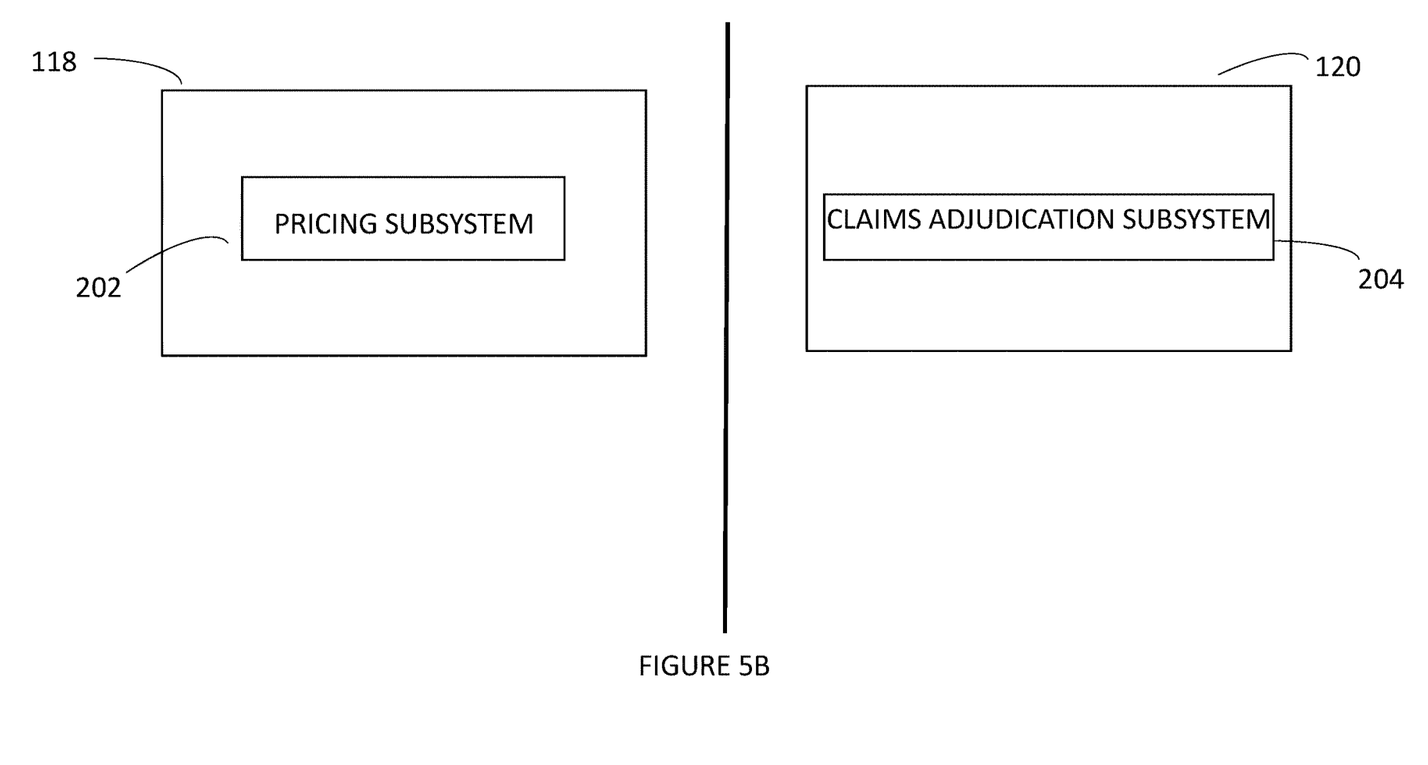
FIG. 5B is a block diagram of an example system, according to an example embodiment which utilizes parallel processing for pharmacy fulfillment.
Figure 5C:
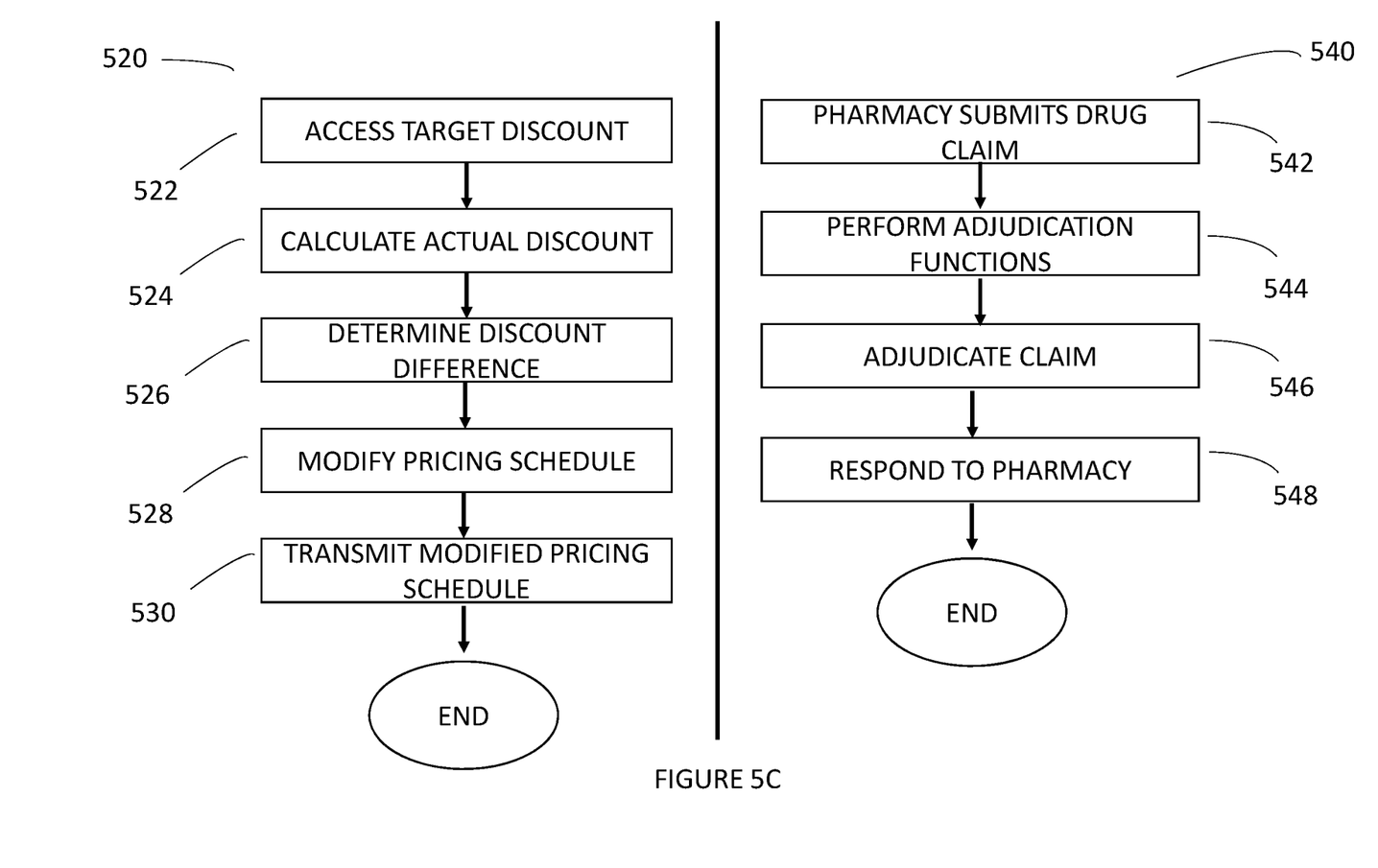
FIG. 5C is a process flow illustrating a method for pharmacy fulfillment that utilizes parallel processing.

Another embodiment of the present disclosure provides for a system and method for pharmacy fulfillment using parallel processing. Such an embodiment is illustrated by FIG. 5B and FIG. 5C. Turning first to FIG. 5B, which is a block diagram of an example system, multiple processors may be used to process different functions of the pharmacy fulfillment process. For example, a first processor 118 and a first memory that is coupled to the first processor may be executed by the pricing subsystem 202. As illustrated in detail in FIG. 4, the pricing subsystem 202 may further comprise a plurality of modules that are executed by the first processor 118.

A target guarantee module 402 may be deployed in the first memory and executed by the first processor 118 to access a plurality of target prescription drug discount guarantees associated with a pharmacy benefit manage client. In one embodiment, a first target prescription drug discount guarantee may be based on an average wholesale price (AWP) of a first plurality of different types of prescription drugs in a first class of prescription drug and a first channel of prescription drug delivery. A second target prescription drug discount guarantee of the plurality of target prescription drug discount guarantees may also be based on an AWP of a second plurality of different types of prescription drugs in a second class of prescription drug and a second channel of prescription drug delivery. The first target prescription drug discount guarantee may be different from the second target prescription drug discount guarantee, and the first class of prescription drug, the first channel of prescription drug delivery, or both the first class of prescription drug and the first channel of prescription drug delivery may be different than the second class of prescription drug, the second channel of prescription drug delivery, or both the second class of prescription drug and the second channel of prescription drug delivery respectively.

A discount module 404 may be deployed in the first memory and executed by the first processor 118 to calculate a first prescription drug discount using a first plurality of adjudicated, prescription drug claims associated with the pharmacy benefit manager client and in the first class of prescription drug and the first channel of prescription drug delivery during a time period to obtain a first calculated prescription drug discount. Calculating the discount may include a total price paid including price paid by the member and an amount by the pharmacy benefit manager client to the pharmacy.

A discount difference module 408 may be deployed in the first memory and executed by the first processor 118 to determine a difference between the first target prescription drug discount guarantee and the calculated first prescription drug discount and a modifier module 412 may be deployed in the first memory and executed by the first processor 118 to modify a prescription drug pricing schedule associated with the pharmacy benefit manager client based on the difference between the first target discount guarantee and the first prescription drug discount to create a modified prescription drug pricing schedule that is used to adjudicate subsequent pharmacy claims.

A second processor 120 and a second memory that is coupled to the second processor may be executed by the claims adjudication subsystem 204. This claims adjudication subsystem 204 may be deployed in the second memory and executed by the second processor 120 to adjudicate a prescription claim from a pharmacy device using an unmodified prescription drug pricing schedule until the modified prescription drug pricing schedule is loaded into the second processor 120.

FIG. 5C illustrates a method for pharmacy fulfillment that utilizes parallel processing. The FIG. 5C illustrates that in this embodiment, two separate processes, one for modifying a prescription pricing schedule 520 and one for adjudicating prescription claims 540, may be run substantially simultaneously. Parallel processing splits the method for pharmacy fulfillment into two parts so that different functions are executed substantially simultaneously on different processors. Such a solution is advantageous over the prior art because it provides for continuous business operations and avoids interruptions that were historically experienced when pharmacy fulfillment was accomplished using methods that did not implement parallel processing.

Methods for pharmacy fulfillment that are run using a single processor configuration require interruption to business operations to update a prescription pricing schedule or adjudicate claims. Given that multiple thousands of claims are processed in a given day, the business cannot afford such interruptions in the systems and must be able to operate the devices and systems continuously and without stopping one critical process to achieve the other.

Using parallel processing eliminates interruptions to the system previously found when modifying prescription pricing schedules using a single processor or configurations that do not implement parallel processing. This results in more efficient system operations, ensuring that pharmacies have the most current pricing schedule without having to interrupting or stopping normal business system operations.

In one example, a first processor may be dedicated to the process for modifying the prescription pricing schedule 520 and a second processor, which is different than the first processor, may be dedicated to the process for adjudicating prescription claims 540. Such a configuration is advantageous over the prior art because it enables each process to run independently and without interruption which in turn results in uninterrupted business system operations.

Turning first to the process for modifying a prescription pricing schedule 520, a plurality of target discount guarantees associated with a client may be accessed at block 522. These discount guarantees may be accessed on a first processor over a network from a database that is separate from the first processor. A first prescription drug discount may be calculated on the first processor at block 524. This discount may be calculated using a first plurality of adjudicated prescription drug claims associated with the pharmacy benefit manager client and in the first class of prescription drug and in the first channel of prescription drug delivery during a certain time period.

A block 526, the method comprises determining, on the first processor, a difference between the first target prescription drug discount guarantee and the calculated first prescription drug discount. The prescription drug schedule may then be modified, again on the first processor, based on the difference determined at block 526. This modified pricing schedule may be used to adjudicate subsequent pharmacy claims. The modified pricing schedule is transmitted in block 530 to a second processor which is utilized for the adjudication process.

Turning now to the process for adjudicating prescription claims 540, a pharmacy may submit a prescription drug claim at block 542. The second processor may perform adjudication functions at block 544 and adjudicate the claim at block 546. This adjudication may be accomplished using an unmodified pricing schedule until the modified pricing schedule created at block 528 is transmitted to and loaded into the second processor. Once the claim is adjudicated, a response may be transmitted by the second processor to the pharmacy at block 548.

Figure 6:
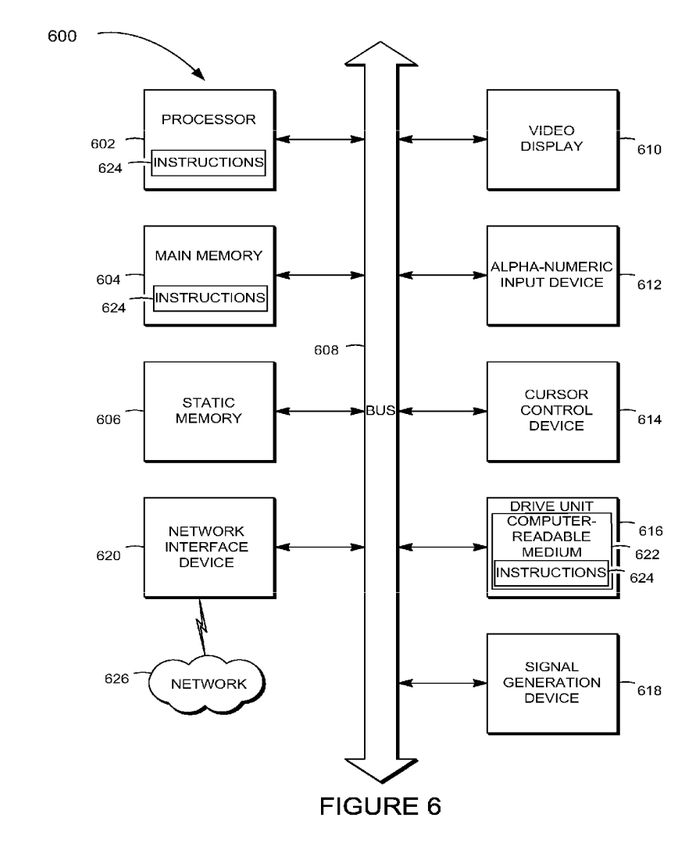
FIG. 6 is a block diagram of a machine in the example form of a computer system within which a set of instructions for causing the machine to perform any one or more of the methodologies discussed herein may be executed or stored.

FIG. 6 shows a block diagram of a machine in the example form of a computer system 600 within which a set of instructions may be executed causing the machine to perform any one or more of the methods, processes, operations, or methodologies discussed herein. The user device 102, and/or the benefit manager device 106 may include the functionality of the one or more computer systems 600.

In an example embodiment, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a server computer, a client computer, a personal computer (PC), a tablet PC, a gaming device, a set-top box (STB), a Personal Digital Assistant (PDA), a cellular telephone, a web appliance, a network router, switch or bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 600 includes a processor 602 (e.g., a central processing unit (CPU) a graphics processing unit (GPU) or both), a main memory 604 and a static memory 606, which communicate with each other via a bus 608. The computer system 600 further includes a video display unit 610 (e.g., a liquid crystal display (LCD) or a cathode ray tube (CRT)). The computer system 600 also includes an alphanumeric input device 612 (e.g., a keyboard), a cursor control device 614 (e.g., a mouse), a drive unit 616, a signal generation device 618 (e.g., a speaker) and a network interface device 620.

The drive unit 616 includes a computer-readable medium 622 on which is stored one or more sets of instructions (e.g., software 624) embodying any one or more of the methodologies or functions described herein. The software 624 may also reside, completely or at least partially, within the main memory 604 and/or within the processor 602 during execution thereof by the computer system 600, the main memory 604 and the processor 602 also constituting computer-readable media.

The software 624 may further be transmitted or received over a network 626 via the network interface device 620.

In an example embodiment, a first system 600 may execute the process 520 and a second system 600 may execute the process 540. The first and second systems 600, 600 may operate in parallel and at times simultaneously.

While the computer-readable medium 622 is shown in an example embodiment to be a single medium, the term "computer-readable medium" should be taken to include a single medium or multiple media (e.g., a centralized or distributed database, and/or associated caches and servers) that store the one or more sets of instructions. The term "computer-readable medium" shall also be taken to include any medium that is capable of storing or encoding a set of instructions for execution by the machine and that cause the machine to perform any one or more of the methodologies of the present invention. The term "computer-readable medium" shall accordingly be taken to include, but not be limited to, solid-state memories, and optical media, and magnetic media. In some embodiments, the computer-readable medium is a non-transitory computer-readable medium.

The term "based on" or using, as used herein, reflects an open-ended term that can reflect others elements beyond those explicitly recited.

Certain systems, apparatus, applications or processes are described herein as including a number of modules. A module may be a unit of distinct functionality that may be presented in software, hardware, or combinations thereof. When the functionality of a module is performed in any part through software, the module includes a computer-readable medium. The modules may be regarded as being communicatively coupled.

The inventive subject matter may be represented in a variety of different embodiments of which there are many possible permutations.

In an example embodiment, a target prescription drug discount guarantee associated with a pharmacy benefit manager client may be accessed. A prescription drug discount associated with a plurality of prescription drug claims associated with the pharmacy benefit manager client may be calculated to obtain a calculated prescription drug discount. A difference between the target prescription drug discount guarantee and the calculated prescription drug discount may be determined. A prescription drug pricing schedule associated with the pharmacy benefit manager client may be modified based on the difference between the target discount guarantee and the prescription drug discount to create a modified prescription drug pricing schedule.

Thus, methods and systems for managing pricing guarantees have been described. Although embodiments of the present invention have been described with reference to specific example embodiments, it will be evident that various modifications and changes may be made to these embodiments without departing from the broader spirit and scope of the embodiments of the invention. Accordingly, the specification and drawings are to be regarded in an illustrative rather than a restrictive sense.

The methods described herein do not have to be executed in the order described, or in any particular order. Moreover, various activities described with respect to the methods identified herein can be executed in serial or parallel fashion. Although "End" blocks are shown in the flowcharts, the methods may be performed continuously.

The Abstract of the Disclosure is provided to comply with 37 C.F.R. § 1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus, the following claims are hereby incorporated into the Detailed Description, with each claim standing on its own as a separate embodiment.

What is claimed is:

1. A pharmacy fulfillment networked parallel processing method comprising:
  performing a predictive modification of a prescription drug pricing schedule, by a first processor of a parallel processing system, by:
    accessing a target discount guarantee associated with a pharmacy benefit manager client, by the first processor over a network, the target discount guarantee being based on an average wholesale price (AWP) of a plurality of different types of prescription drugs in a first class of prescription drug and a first channel of prescription drug delivery;
    calculating an actual prescription drug discount using a plurality of adjudicated prescription drug claims for a first time period, by the first processor, the plurality of adjudicated prescription drug claims being associated with the pharmacy benefit manager client and in the first class of prescription drug and the first channel of prescription drug delivery during the first time period predicting at least one prescription rate change for prescription drugs included in the target discount guarantee, for an anticipated future time period, by the first processor, to generate at least one predicted prescription rate change, based on one or more of: historical adjudicated claims data, seasonal prescription rate data, anticipated new drug release data, and prescription drug patent expiration data;

modifying the prescription drug pricing schedule associated with the pharmacy benefit manager client, by the first processor, based on the at least one predicted prescription rate change and a difference between the target discount guarantee and the actual prescription drug discount, to create a modified prescription drug pricing schedule; and loading the modified prescription drug pricing schedule into a second processor of the parallel processing system, by the first processor;

adjudicating prescription claims using an unmodified prescription drug pricing schedule until loading of the modified prescription drug pricing schedule, by the second processor operating in parallel to the first processor, wherein the first processor and the second processor operate simultaneously and continuously; and in response to the loading,
replacing the unmodified prescription drug pricing schedule with the modified prescription drug pricing schedule; and using the modified prescription drug pricing schedule to adjudicate subsequent prescription claims, by the second processor operating in parallel to the first processor.

2. The method of claim 1, wherein accessing the target discount guarantee associated with the pharmacy benefit manager client further comprises:
accessing contract data associated with the pharmacy benefit manager client; and
determining the target discount guarantee based on the contract data.

3. The method of claim 1, wherein calculating the prescription drug discount further comprises:
identifying a plurality of excluded prescription drug claims among the plurality of adjudicated, prescription drug claims from the target discount guarantee; and
calculating the prescription drug discount from the plurality of adjudicated, prescription drug claims that are not identified as being among the plurality of excluded prescription drug claims to obtain the calculated prescription drug discount.

4. The method of claim 3, wherein identifying the plurality of excluded prescription drug claims further comprises accessing an exclusion profile associated with the pharmacy benefit manager client, where the exclusion profile includes identification of a type of prescription drug, a class of prescription drug, a specific prescription drug, or combinations thereof excluded from the target discount guarantee.

5. The method of claim 4, further comprising modifying the exclusion profile associated with the pharmacy benefit manager client.

6. The method of claim 5, further comprising accessing exclusion data associated with exclusion of a particular prescription drug from the plurality of prescription drugs based on classification of the particular prescription drug as being a single source generic prescription drug, wherein modifying the exclusion profile is based on access of the exclusion data.

7. The method of claim 6, wherein accessing exclusion data further comprises receiving an exclusion notification of a particular prescription drug from the plurality of prescription drugs based on classification of the particular prescription drug as being a single source generic prescription drug, wherein modifying the exclusion profile is based on receipt of the exclusion notification.

8. The method of claim 6, wherein accessing exclusion data further comprises classifying a particular prescription drug from the first plurality of adjudicated, prescription drugs as being a single source generic prescription drug, wherein modifying the exclusion profile is based on classification of the particular prescription drug.

9. The method of claim 1, further comprising:
transmitting a difference notification based on the difference between the target discount guarantee and the actual discount; and
receiving an approval to modify the prescription drug pricing schedule in response to transmission of the difference notification, wherein modifying the prescription drug pricing schedule is in response to receipt of the approval.

10. The method of claim 1, wherein modifying the prescription drug pricing schedule further comprises:
identifying a plurality of excluded prescription drugs; and
modifying a price on the prescription drug pricing schedule of a prescription drug of the first plurality of adjudicated, prescription drug claims, the prescription drug not being an excluded drug.

11. The method of claim 1, further comprising transmitting the modified pricing schedule to a claims adjudication system on the second processor.

12. The method of claim 1, wherein the prescription claim further comprises a prescription claim for a tangible prescription drug as part of a plurality of prescriptions covered in an individual pricing schedule for one of a plurality of pharmacy benefit manager clients.

13. The method of claim 1, wherein modifying the prescription drug pricing schedule further comprises:
transmitting a difference notification based on the difference between the target discount guarantee and the actual discount;
displaying both the target discount guarantee and the actual discount as a subset of the prescription drug pricing schedule; and
receiving an approval to modify the prescription drug pricing schedule in response to transmission of the difference notification and display of the target discount guarantee and the actual discount, wherein modifying the prescription drug pricing schedule is in response to receipt of the approval.

14. The method of claim 13, further comprising transmitting the modified prescription drug pricing schedule to the database to store the modified prescription drug pricing schedule and to a remote device to display the modified prescription drug pricing schedule.

15. The method of claim 14, further comprising replacing the prescription drug pricing schedule with the modified prescription drug pricing schedule.

16. The method of claim 1, further comprising tracking a channel of delivery of prescription drugs to determine the first channel of prescription drug delivery and the second channel of prescription drug delivery.

17. The method of claim 1, further comprising classifying the prescription drugs into classes including the first class of prescription drug and the second class of prescription drug.

18. The method of claim 1, further comprising:
accessing claims data for the first time period, by the first processor over the network, the claims data indicating a prescription drug associated with adjudicated claims for the first time period, and a number of adjudications for the prescription drug during the first time period;
determining a rate of adjudication for the prescription drug, based on the number of adjudications during the first time period;
determining a second rate of adjudication for the anticipated future time period, the second rate varying in a pattern over time based on at least one of the historical adjudicated claims data, the seasonal prescription rate data, the anticipated new drug release data, and the prescription drug patent expiration data; and
predicting the at least one prescription rate change based on the rate of adjudication for the first time period and the second rate of adjudication for the anticipated future time period.

19. The method of claim 1, further comprising:
accessing claims data for the first time period, by the first processor over the network, the claims data indicating a prescription drug associated with adjudicated claims for the first time period, and a number of adjudications for the prescription drug during the first time period;
determining a rate of adjudication for the prescription drug, based on the number of adjudications during the first time period;
determining a second rate of adjudication for the anticipated future time period, the second rate being constant over time based on at least one of the historical adjudicated claims data, the anticipated new drug release data, and the prescription drug patent expiration data; and
predicting the at least one prescription rate change based on the rate of adjudication for the first time period and the second rate of adjudication for the anticipated future time period.

20. A non-transitory machine-readable medium comprising instructions, which, when executed by one or more processors, cause the one or more processors to perform the following operations:
perform a predictive modification of a prescription drug pricing schedule, by a first processor of a parallel processing system for pharmacy fulfillment, by:
accessing a target discount guarantee associated with a pharmacy benefit manager client, by a first processor over a network the target discount guarantee being based on an average wholesale price (AWP) of a plurality of different types of prescription drugs in a first class of prescription drug and a first channel of prescription drug delivery;
calculating an actual discount using a plurality of adjudicated prescription drug claims for a first time period, by the first processor, the plurality of adjudicated prescription drug claims being associated with the pharmacy benefit manager client and in the first class of prescription drug and the first channel of prescription drug delivery during the first time period;
predicting at least one prescription rate change for prescription drugs included in a target discount guarantee, for an anticipated future time period, by the first processor, to generate at least one predicted prescription rate change, based on one or more of: historical adjudicated claims data, seasonal prescription rate data, anticipated new drug release data, and prescription drug patent expiration data;
modifying the prescription drug pricing schedule associated with the pharmacy benefit manager client, by the first processor, based on the at least one predicted prescription rate change and a difference between the target discount guarantee and the actual discount to create a modified prescription drug pricing schedule; and
loading the modified prescription drug pricing schedule into a second processor of the parallel processing system, by the first processor;
adjudicate prescription claims using an unmodified prescription drug pricing schedule until loading of the modified prescription drug pricing schedule, by the second processor operating in parallel to the first processor, wherein the first processor and the second processor operate simultaneously and continuously; and
in response to the loading,
replace the unmodified prescription drug pricing schedule with the modified prescription drug pricing schedule; and
use the modified prescription drug pricing schedule to adjudicate subsequent prescription claims, by the second processor operating in parallel to the first processor.

21. The non-transitory machine-readable medium of claim 20, wherein the instructions to access the target discount guarantee associated with the pharmacy benefit manager client further comprise instructions to:
access contract data associated with the pharmacy benefit manager client; and determine the target discount guarantee based on the contract data.

22. The non-transitory machine-readable medium of claim 20, wherein the instructions to access the target discount guarantee associated with the pharmacy benefit manager client further comprise instructions to:
identify a plurality of excluded prescription drug claims among the first plurality of adjudicated, prescription drug claims from the first target discount guarantee; and
calculate the actual discount from the first plurality of adjudicated prescription drug claims that are not identified as being among the plurality of excluded prescription drug claims to obtain the actual discount.

23. The non-transitory machine-readable medium of claim 20, wherein the instructions to access the target discount guarantee associated with the pharmacy benefit manager client further comprise instructions to access an exclusion profile associated with the pharmacy benefit manager client, the exclusion profile including identification of a type of prescription drug, a class of prescription drug, a specific prescription drug, or combinations thereof excluded from the target discount guarantee.

24. A pharmacy fulfillment networked parallel processing system comprising:
a first processor and a first memory coupled to the first processor, the first processor configured to perform a predictive modification of a prescription drug pricing schedule via a target guarantee module, a discount module, a predictive analytics module, and a modifier module;

a second processor and a second memory coupled to the second processor, wherein the second processor is separate from the first processor;

the target guarantee module deployed in the first memory and executed by the first processor to access a target discount guarantee associated with a pharmacy benefit manager client, the target discount guarantee being based on an average wholesale price (AWP) of a plurality of different types of prescription drugs in a first class of prescription drug and a first channel of prescription drug delivery;

the discount module deployed in the first memory and executed by the first processor to calculate an actual discount using a plurality of adjudicated prescription drug claims for a first time period, by the first processor, the plurality of adjudicated prescription drug claims being associated with the pharmacy benefit manager client and in the first class of prescription drug and the first channel of prescription drug delivery during the first time period;

the predictive analytics module deployed in the first memory and executed by the first processor to predict at least one prescription rate change for prescription drugs included in the target discount guarantee, for an anticipated future time period, by the first processor, to generate at least one predicted prescription rate change, based on one or more of: historical adjudicated claims data, seasonal prescription rate data, anticipated new drug release data, and prescription drug patent expiration data;

the modifier module deployed in the first memory and executed by the first processor to modify the prescription drug pricing schedule associated with the pharmacy benefit manager client, by the first processor, based on the at least one predicted prescription rate change and a difference between the target discount guarantee and the actual discount, to create a modified prescription drug pricing schedule;

a loader module deployed in the first memory and executed by the first processor to load the modified prescription drug pricing schedule into a second processor of the parallel processing system, by the first processor;

a claims adjudication subsystem deployed in the second memory and executed by the second processor to adjudicate prescription claims using an unmodified prescription drug pricing schedule until loading of the modified prescription drug pricing schedule, by the second processor operating in parallel to the first processor, wherein the first processor and the second processor operate simultaneously and continuously; and a claims adjudication system update module deployed in the second memory and executed by the second processor, in response to the loading, to replace the unmodified prescription drug pricing schedule with the modified prescription drug pricing schedule;

wherein the claims adjudication subsystem uses the modified prescription drug pricing schedule to adjudicate subsequent prescription claims, by the second processor operating in parallel to the first processor.

25. A pharmacy fulfillment networked parallel processing method comprising:

performing a predictive modification of a prescription drug pricing schedule, by a first processor of a parallel processing system, by:

storing, in a database, a channel of delivery of prescription drugs to determine a first channel of prescription drug delivery;

classifying the prescription drugs into classes including first class of prescription drug;

setting a target discount guarantee associated with a pharmacy benefit manager client, by the first processor over a network, the target discount guarantee being based on an average wholesale price (AWP) of a plurality of different types of prescription drugs in the first class of prescription drug and the first channel of prescription drug delivery;

retrieving, by a first processor over the network from a database separate from the first processor, the target discount guarantee;

calculating an actual discount using a plurality of adjudicated prescription drug claims for a first time period, by the first processor, the plurality of adjudicated prescription drug claims being associated with the pharmacy benefit manager client and in the first class of prescription drug and the first channel of prescription drug delivery during the first time period;

predicting at least one prescription rate change for prescription drugs included in the target discount guarantee, for an anticipated future time period, by the first processor, to generate at least one predicted prescription rate change, based on one or more of: historical adjudicated claims data, seasonal prescription rate data, anticipated new drug release data, and prescription drug patent expiration data;

modifying the prescription drug pricing schedule associated with the pharmacy benefit manager client, by the first processor, based on the at least one predicted prescription rate change and a difference between the target discount guarantee and the actual discount to create a modified prescription drug pricing schedule, wherein modifying includes:

transmitting a difference notification based on the difference between the first target discount guarantee and the actual discount; and receiving an approval to modify the prescription drug pricing schedule in response to transmission of the difference;

wherein modifying the prescription drug pricing schedule is in response to receipt of the approval;

transmitting the prescription drug pricing schedule to a remote device to display the prescription drug pricing schedule;

transmitting the modified prescription drug pricing schedule to the database to store the modified prescription drug pricing schedule and to the remote device to display the modified prescription drug pricing schedule and replace the prescription drug pricing schedule; and adjudicating, on a second processor separate from the first processor in parallel with modifying the prescription drug pricing schedule, a prescription claim for a tangible prescription drug as part of plurality of prescriptions covered in an individual pricing schedule for one of a plurality of pharmacy benefit manager clients from a pharmacy device on a second processor, which is separate from the first processor and the database, using an unmodified prescription drug pricing schedule until loading of the modified prescription drug pricing schedule is loaded into the second processor operating in parallel to the first processor, wherein the first processor and the second processor operate simultaneously and continuously;

in response to the loading,
  replacing the unmodified prescription drug pricing schedule with the modified prescription drug pricing schedule; and
  using the modified prescription drug pricing schedule to adjudicate subsequent prescription claims, by the second processor operating in parallel to the first processor.

26. The method of claim 25, wherein retrieving the target discount guarantee associated with the pharmacy benefit manager client comprises:
  accessing contract data associated with the pharmacy benefit manager client; and
  determining the target discount guarantee based on the contract data.

27. The method of claim 26, wherein calculating the actual discount comprises:
  identifying a plurality of excluded prescription drug claims among the first plurality of adjudicated, prescription drug claims from the target discount guarantee; and
  calculating the actual discount from the first plurality of adjudicated, prescription drug claims that are not identified as being among the plurality of excluded prescription drug claims to obtain the actual discount.

28. The method of claim 27, wherein identifying the plurality of excluded prescription drug claims comprises:
  accessing an exclusion profile associated with the pharmacy benefit manager client, the exclusion profile including identification of a type of prescription drug, a class of prescription drug, a specific prescription drug, or combinations thereof excluded from the target discount guarantee.

29. The method of claim 28, further comprising:
  modifying the exclusion profile associated with the pharmacy benefit manager client.

30. The method of claim 29, further comprising:
  accessing exclusion data associated with exclusion of a particular prescription drug from the plurality of executed prescription drugs based on classification of the particular prescription drug as being a single source generic prescription drug,
  wherein modifying the exclusion profile is based on access of the exclusion data.

31. The method of claim 30, wherein accessing exclusion data comprises:
  receiving an exclusion notification of the particular prescription drug from the plurality of executed prescription drugs based on classification of the particular prescription drug as being a single source generic prescription drug,
  wherein modifying the exclusion profile is based one receipt of the exclusion notification.

* * * * *